United States Patent [19]

Sanchez

[11] 4,050,459
[45] Sept. 27, 1977

[54] HYPODERMIC SYRINGE

[76] Inventor: Anacleto Montero Sanchez, Maria Auxiliadora 35, Salamanca, Spain

[21] Appl. No.: 688,193

[22] Filed: May 20, 1976

[30] Foreign Application Priority Data

May 23, 1975 Spain .................... 212610

[51] Int. Cl.² ............................................. A61M 5/00
[52] U.S. Cl. .............................. 128/218 C; 128/234
[58] Field of Search ......... 128/218 P, 218 PA, 218 R, 128/218 C, 215, 216, 234

[56] References Cited

U.S. PATENT DOCUMENTS

| | | | |
|---|---|---|---|
| 1,393,720 | 10/1921 | Lomas et al. ..................... | 128/234 |
| 2,844,148 | 7/1958 | Raife ............................... | 128/218 C |
| 2,875,761 | 3/1959 | Helmer et al. .................... | 128/218 C |

FOREIGN PATENT DOCUMENTS

| | | | |
|---|---|---|---|
| 1,156,298 | 5/1958 | France ............................ | 128/218 C |
| 1,186,571 | 4/1959 | France ............................ | 128/218 C |
| 542,130 | 4/1956 | Italy .............................. | 128/218 C |
| 6,908,371 | 12/1970 | Netherlands ...................... | 128/218 C |

*Primary Examiner*—John D. Yasko
*Attorney, Agent, or Firm*—Nolte and Nolte

[57] ABSTRACT

A hypodermic syringe for administering a plurality of measured doses, particularly to animals, comprises a barrel and a plunger movable in the barrel, the plunger having a track and the barrel a track follower. The track is made up of a plurality of stages each stage corresponding to a movement in the plunger which will expel from the syringe a single dose.

5 Claims, 3 Drawing Figures

HYPODERMIC SYRINGE

BACKGROUND OF THE INVENTION

This invention is concerned with a hypodermic syringe, particularly, but not necessarily exclusively, it is concerned with a syringe for use by a veterinarian in injecting various medications into an animal. It is to be recognized that the term "medication" is used herein to mean the various substances which are commonly injected by hypodermic syringe, as for example, anaesthetics, antibiotics and vaccines, etc.

It is an object of the present invention to provide an hypodermic syringe from which a plurality of measured amounts or doses of medication may be dispensed from a single filling of the syringe. It is a further object of the present invention to provide such a syringe in which a plurality of doses can be dispensed without having to re-load the syringe after each use, or to carefully measure the travel of the plunger against a graduated scale.

BRIEF SUMMARY OF THE INVENTION

According to this invention, there is provided a hypodermic syringe comprising a barrel and plunger movable within the barrel to dispense medication. The barrel or the plunger is provided with a track and the other of the barrel and plunger is provided with track follower means, the track being in stages extending axially of the barrel and plunger, each stage corresponding to a travel of the plunger equal to that which will dispense a known dose of the medication. In one form of the invention the track comprises a step-like groove with risers extending axially along a surface of the plunger and tread sections extending circumferentially of the plunger. In such an arrangement the track follower comprises a projection on the barrel adapted to engage in the track. Movement of the plunger over one riser section will cause a predetermined dose of medication to be dispensed from the syringe thereafter the plunger may be turned so the follower moves along a tread section of the track to align with another riser section and dispense a further dose.

DESCRIPTION OF THE PREFERRED EMBODIMENTS

Figure 1:
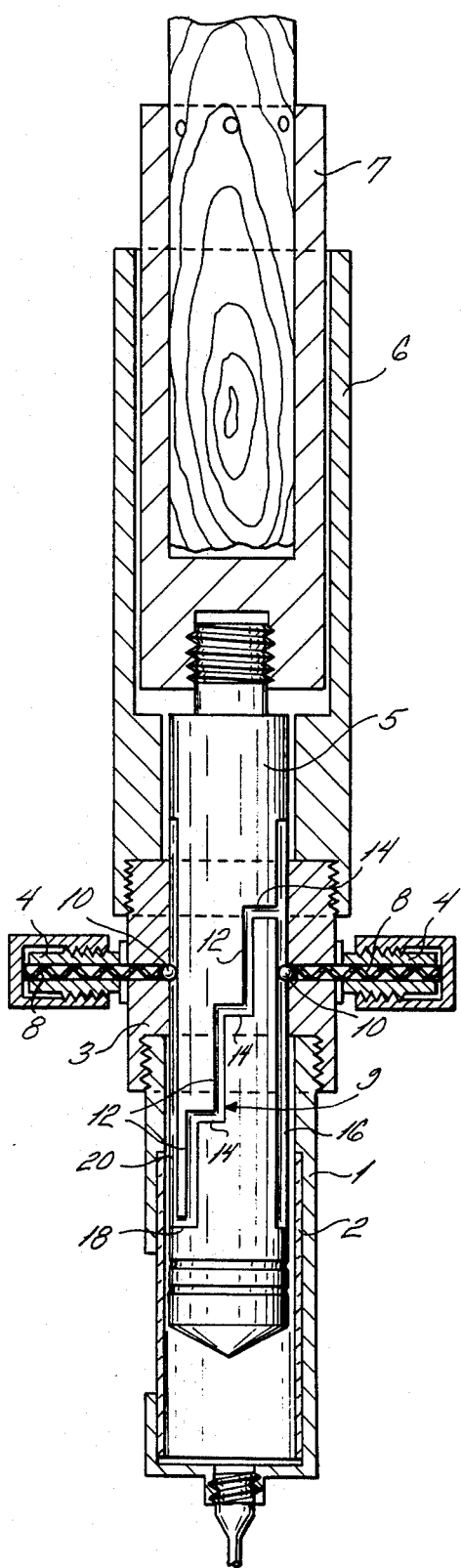
FIG. 1 illustrates, schematically, in cross section, one embodiment of the invention.
Figure 3:
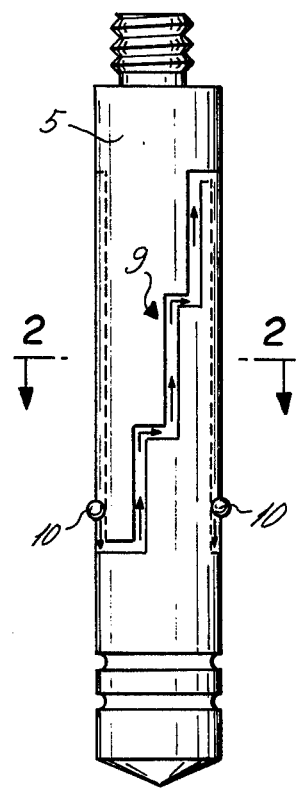
FIG. 3 is a detail of the embodiment of FIG. 1.
Figure 2:
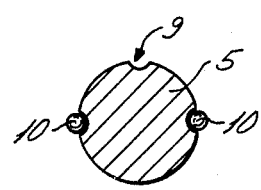
FIG. 2 is a cross section along the line A—A' of FIG. 3.

The syringe of the drawings comprises a barrel formed by a front, tube supporting section 1 which supports a transparent medication containing tube 2 and has a screwthreaded fitment at its lowermost end (considered as shown in the drawings) for receiving a needle and has at its opposite end a further screw threaded portion upon which an intermediate section 3 is received. The upper end of the intermediate section 3 is similarly screw-threaded for reception of a guide section 6.

Disposed for sliding movement within the barrel is a plunger 5 having a threaded extension at its upper end for receiving a corresponding configuration of an operating element 7. Secured to and extending radially from intermediate section 3 are a pair of diametrically opposed projections 4 which have central passages which register with radial passages in the intermediate section 3. Disposed in those passages is a spring 8 and ball 10, the spring working between the ball and the base of a cap threadedly received upon the projections 4. In this way the ball urged radially inwardly of the syringe to engage, in a manner described hereinafter, with a track formed on the outer cylindrical surface of plunger 5 to be constituted as track follower means.

On the outer cylindrical surface of the plunger there is a step-like track 9 which comprises axially extending riser sections 12, adjacent ends of which are connected by tread sections 14 which extend circumferentially of the surface of the plunger.

The uppermost of the riser sections 12 is extended as at 16 for a purpoe described in detail hereinafter. Also the lowermost riser section 12 has, at its lower end, a tread section 18 which leads to an axially extending track section 20 diametrically opposed to track section 16. Track section 16 and the riser section 12 with which it is aligned and track section 20 both extend over the full travel of the plunger.

In FIG. 1 of the drawings the syringe is shown in an attitude which it would have while the syringe is being filled. At this stage, the two balls 10 are in track sections 16 and 18 and the plunger is drawn upwardly and away from the needle to draw medication, through the needle, into the volume of the barrel in front of the plunger head. When the syringe is filld, the balls will be at the lowermost portions of the track sections 16 and 20, respectively. The plunger is then turned so that the ball at the left hand side of FIG. 1 will traverse tread section 18 to reach the lowermost portion of the lower riser section 12 while the ball at the right hand side of FIG. 1 will be retracted against the action of spring 8 to move against the outer surface of the plunger. The plunger may then be moved towards the needle until such time as the left hand ball reaches the upper end of the lower riser section of the track. The riser section is of a length to represent the movement of the plunger to dispense a predetermined dose of medication, generally 2 or 5 cm.

To dispense a further measured dose, the plunger is once more rotated relative to the barrel so that the left hand ball 10 moves along the lowermost of the tread sections 14 to the bottom of the next riser section. The plunger can then be advanced in the same manner as herebefore described to dispense the second dose. This process is repeated until all doses are dispensed. When the last dose has been dispensed the left hand one of the balls 10, as viewed in FIG. 1, will be engaged in track section 16 and, of course, the right hand ball will be disposed in track section 20. In this position the syringe may be refilled and the above dispensing procedure repeated.

It is also, of course, to be recognized that the full contents of the syringe may be dispensed in one movement, simply by failing to turn the plunger before the initial dose is given so that as the plunger is advanced it may travel with the balls in track section 16 and 20 from top to bottom of those track sections.

It is to be appreciated that the present invention is subject to various alterations which do not deviate from its scope. For example, in particular it will be recognized that the track could be formed on the surface of the barrel while the plunger could have track follower means. It should also be recognized that the various elements which go up to make the barrel and the plunger could be varied well within the scope of the present invention. Additionally, the plunger will, of course, be provided with conventional sealing O-rings and other necessary parts which do not, per se, form a part of the present invention and are omitted on the specific description merely in the interests of clarity.

What is claimed is:

1. A hypodermic syringe comprising a barrel and a plunger slidably and rotatably received in said barrel, said barrel and plunger having cooperating cylindrical surfaces, one of said surfaces having track means comprising a circumferential section and two axially extend and radially off-set sections, adjacent terminal portions of said axial section being connected by said circumferential section and said axial sections extending in opposite axial directions from said circumferential section, and track follower means on the other of said surfaces, whereby said plunger may be moved axially in said barrel with said track follower means engaging a first axial section of said track and thereafter moved further axially with said track follower means engaging said other axial track section to dispense, sequentially, doses of a medication in amounts related to the lengths of said track sections, said track follower means comprising a ball engaging in said track and spring means urging said ball radially into engagement with said track.

2. A hypodermic syringe comprising a barrel and a plunger slidably and rotatably received in said barrel, said barrel and plunger having cooperating cylindrical surfaces, one of said surfaces having step-like track means comprising circumferentially extending tread sections and axially extending riser sections and the other of said surfaces having track follower means engaging said track means to guide said plunger in step-like movement in said barrel, said track follower means comprising a ball engaging in said track and spring means urging said ball radially into engagement with said track.

3. A syringe as claimed in claim 1 wherein said track means further comprises a track section extending wholly axially along said surface and over a distance equal to that covered by said axial sections, whereby the entire contents of said syringe may be dispensed as a single dose by moving said track follower means within said wholly axially extending section.

4. A syringe as claimed in claim 1 wherein said track means comprises a step-like track formed as a groove in said surface of said plunger.

5. A syringe as claimed in claim 2 wherein said track means extend around one-half of the circumference of said surface and said track follower means comprises two diametrically opposed elements, at least one of which always engages said track.

* * * * *